United States Patent [19]

Cohen et al.

[11] Patent Number: 5,674,875
[45] Date of Patent: Oct. 7, 1997

[54] METHOD OF BLOCKING HUMAN 5-HYDROXYTRYPTAMINE-2 RECEPTORS

[75] Inventors: Marlene L. Cohen; David L. G. Nelson, both of Carmel, Ind.

[73] Assignee: Eli Lilly and Company, Indianapolis, Ind.

[21] Appl. No.: 389,515

[22] Filed: Feb. 16, 1995

Related U.S. Application Data

[63] Continuation of Ser. No. 57,223, May 4, 1993, abandoned.
[51] Int. Cl.$^6$ .................................................. A61K 31/44
[52] U.S. Cl. .................................................... 514/288
[58] Field of Search ........................................ 514/288

[56] References Cited

U.S. PATENT DOCUMENTS

| | | |
|---|---|---|
| 2,736,728 | 2/1956 | Pioch . |
| 2,774,763 | 12/1956 | Garbrecht . |
| 4,798,834 | 1/1989 | Merritt et al. . |
| 5,141,944 | 8/1992 | Cohen et al. . |

FOREIGN PATENT DOCUMENTS 816273  7/1959  United Kingdom .

OTHER PUBLICATIONS

Pazos et al, *European Journal of Pharmacology*, 106, 531–538 (1985).
M.P. Johnson, Slide Presentation at Burroughs Wellcome Research Triangle Park, North Carolina, May 3–4, 1992.
Nelson et al. *J. Pharmacol. & Exp. Therapeutics*, 1993, 265(3), 1272–9.
Misner et al. *J. Med. Chem.*, 1990, 33, 652.
Kao et al., Federation of European Biochemical Societies, 307(3) 324 (1992).

*Primary Examiner*—Marianne M. Cintins
*Assistant Examiner*—M. Moezle
*Attorney, Agent, or Firm*—Arleen Palmberg

[57] ABSTRACT

N-unsubstituted ergolines specifically bind to human 5-HT$_2$ receptors, and are thus useful in treating diseases such as depression, hypertension and migraine.

2 Claims, No Drawings

METHOD OF BLOCKING HUMAN 5-HYDROXYTRYPTAMINE-2 RECEPTORS

CROSS REFERENCE TO RELATED APPLICATION

This application is a continuation of application Ser. No. 08/057,223, filed on May 4, 1993 now abandoned.

BACKGROUND OF THE INVENTION

1. Technical Field

This invention is directed to a method of blocking human $5HT_2$ receptors, thereby treating and preventing diseases such as depression, migraine, anxiety and eating disorders. The method comprises administering a 1-unsubstituted ergoline.

2. Background Art

Blocking serotonin receptors has been shown to result in a number of beneficial pharmacological effects, including reduction in disease states such as hypertension, depression, anxiety and the like; see U.S. Pat. No. 5,141,944. Nelson et al., *Psychopharmacology and Biochemistry of Neurotransmitter Receptors*, eds. H. I. Yamamura et al., Elsevier/North Holland Inc., p. 325, have confirmed there are multiple serotonin recognition sites. The general class of serotonin receptors are referred to as 5-HT receptors, and specific sites include $5\text{-HT}_1$, $5\text{-HT}_2$, and $5\text{-HT}_{1C}$ sites. Different physiological effects are believed to be mediated by these different specific serotonin recognition sites. Blocking the human $5\text{-HT}_2$ receptor is believed to result in beneficial effects on disease states such as hypertension, ischemia, depression, schizophrenia, sleep disorders and the like.

Pazos et al., *European Journal of Pharmacology*, 106 (1985) 531-538, established that, while most animals have $5\text{-HT}_2$ receptor sites, these receptors show different pharmacological profiles in different species, such as rat, pig, monkey and human. Accordingly, there is not a direct correlation between animal studies of $5\text{-HT}_2$ antagonists and human utility. We have now surprisingly found a series of ergoline compounds which demonstrate excellent binding activity to human $5\text{-HT}_2$ receptors, with only minimal binding activity in animal species. It is therefore an object of this invention to provide a method of blocking human $5\text{-HT}_2$ receptors with a series of compounds uniquely suited to human treatment.

SUMMARY OF THE INVENTION

This invention provides a method of treating a number of disease states in humans associated with the $5\text{-HT}_2$ receptor sites in the brain tissue and throughout the body. The invention provides a method for selectively blocking the $5\text{-HT}_2$ receptor sites in humans by administering an N-unsubstituted ergoline of the formula

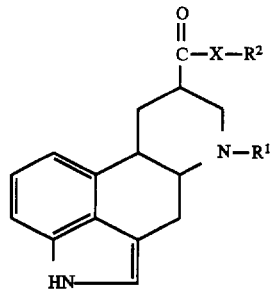

wherein:
$R^1$ is $C_1\text{-}C_4$ alkyl or allyl;
X is O or $NR^3$;
$R^3$ is hydrogen or $C_1\text{-}C_4$ alkyl;
$R^2$ is $C_1\text{-}C_7$ alkyl, hydroxy $C_1\text{-}C_4$ alkyl, $C_3\text{-}C_7$ cycloalkyl, and $C_3\text{-}C_7$ cycloalkyl substituted with hydroxy or methoxy, and pharmaceutically acceptable acid addition salts thereof.

The compounds utilized in the present method are named as ergoline derivatives. The compounds are carboxylic acid esters when X is O, and carboxamides when X is $NR^3$. Typical compounds which can be utilized include:

N-cycloheptyl-6-ethylergoline-8-carboxamide
N-4-methoxycyclopentyl-6-allylergoline-8-carboxamide
N-2-hydroxycyclopropyl-6-isopropylergoline-8-carboxamide
N-2-hydroxyethyl-6-methylergoline-8-carboxamide hydrochloride
N-methoxymethyl-6-n-butylergoline-8-carboxamide oxalate
N-tert.-butyl-6-isopropylergoline-8-carboxamide tartrate
cyclopentyl-6-methylergoline-8-carboxylate
2-hydroxycyclohexyl-6-ethylergoline-8-carboxylate hydrobromide
2-methoxycycloheptyl-6-isobutylergoline-8-carboxylate citrate
cyclohexyl-6-5-propylergoline-8-carboxylate maleate
ethyl-6-methylergoline-8-carboxylate acetate
tert.-butyl-6-methylergoline-8-carboxylate
4-isopropylcyclohexyl-6-allylergoline-8-carboxylate.

The compounds utilized in the present method are either known in the art or are readily available by routine synthetic processes. For instance, Semonsky et al., U.K. Patent No. 816,273 (Jul. 8, 1959) describe a process for making cycloamides of lysergic acid. Other methods for preparing lysergic acid amides are described in U.S. Pat. Nos. 2,736,728 and 2,774,763.

The N-unsubstituted ergolines utilized in the present method have been shown to selectively bind to the $5\text{-HT}_2$ receptor to a surprisingly greater extent than corresponding N-substituted ergolines. This is quite surprising in light of the N-substituted ergolines having a much greater affinity for the $5\text{-HT}_2$ receptors in rats compared to the corresponding N-unsubstituted ergolines. These differences in binding activities were established in in vitro studies utilizing cells contianing cloned human $5\text{-HT}_2$ receptor (prepared by the method of Kao et al., *Febs. Lett*, 307:324-328, 1992. The tests also utilized brain tissues taken from male Sprague-Dawley rats. Binding assays were automated with a Biomek 1000 (Beckman Instruments, Fullerton, Calif.), and were performed in triplicate in 0.8 ml total volume containing 200 µl membrane suspension (approximately 2.5 million cells)

and 200 μl of drug dilution in water. The binding activity is reported as $IC_{50}$ in nM. Data for representative compounds is presented in Table I below.

TABLE I

Compound Tested

| X | $R_2$ | $IC_{50}$ Rat | $IC_{50}$ Human |
|---|---|---|---|
| NH | 2-hydroxycyclopentyl | 64.4 | 2.9 |
| NH | cyclohexyl | 41.6 | 1.9 |
| O | 4-methoxycyclohexyl | 42.0 | 2.8 |

| X | $R_2$ | $IC_{50}$ Rat | $IC_{50}$ Human |
|---|---|---|---|
| NH | 2-hydroxycyclopropyl | 5.8 | 27.7 |
| NH | cyclohexyl | 6.9 | 42.1 |
| O | 4-methoxycyclohexyl | 10.9 | 56.9 |

The data above establish that $N_1$-unsubstituted ergolines have a much higher affinity for human receptors than the corresponding $N_1$-substituted ergolines. This result is opposite to that observed in the rat 5-$HT_2$ receptor. The data thus establish that N-unsubstituted ergolines are surprisingly effective in blocking human 5-$HT_2$ receptors.

As such, this invention provides a method of blocking 5-$HT_2$ receptors which comprises administering to a mammal having an excess of serotonin centrally or peripherally a 5-$HT_2$ blocking dose of an N-unsubstituted ergoline of the above formula. This method is potentially useful in treating disease states in which an excess of circulating serotonin is a major contributing cause. These disease states include hypertension, thrombosis, migraine, vasospasm (both coronary and cerebral), ischemia, depression, anxiety, sleep disorders and appetite disorders.

The compounds of the invention show relatively slight affinity for other receptors such as $\alpha_1$, $\alpha_2$, $\beta$, histamine, carbachol and the like receptors, and thus are highly selective in their action. In mammals, hypertension may be mediated through 5-$HT_2$ receptors. Thus, compounds of the invention will lower blood pressure in humans as does ketanserin, another 5-$HT_2$ blocker, but without the side effects attributable to alpha adrenergic receptor blockage of ketanserin.

In carrying out the methods of the invention, a compound of the invention is administered orally or parenterally to a mammal with an excess of circulating serotonin, in which mammal it is desirable to block 5-$HT_2$ receptors in order to alleviate symptoms attributable to excessive serotonin levels such as high blood pressure and migraine. For parenteral administration, a water soluble salt of the drug is dissolved in an isotonic salt solution and administered by the intravenous route. For oral administration, a pharmaceutically-acceptable salt of the drug is mixed with standard pharmaceutical excipients such as starch and loaded into capsules or made into tablets, each containing about 0.1 to about 100 mg of active drug. The compounds can be formulated into topical patches for transdermal administration. Dosage levels of from about 0.01–1000 mg/kg are effective in blocking 5-$HT_2$ receptors. Thus, the oral dosage would be administered 2–4 times per day, giving a daily dosage range of about 0.003 to about 10.0 mg/kg per day.

We claim:

1. A method of blocking human $5HT_2$ receptors which comprises administering to a human having an excess of serotonin centrally or peripherally a 5-$HT_2$ blocking dose of N-cyclohexyl-6-methylergoline-8-carboxamide.

2. A method of blocking human 5-$HT_2$ receptors which comprises administering to a human having an excess of serotonin centrally or peripherally a 5-$HT_2$ blocking dose of (4-methoxycyclohexyl)-6-methylergoline-8-carboxylate.

* * * * *